(12) United States Patent
Allen et al.

(10) Patent No.: US 8,335,654 B2
(45) Date of Patent: Dec. 18, 2012

(54) METHOD OF GENERATING AN IDENTIFICATION ELEMENT

(75) Inventors: Patrick N. Allen, Boulder, CO (US);
Lawrence R. Ganeshalingam, Dublin, CA (US)

(73) Assignee: JPL Innovations, LLC, Dover, DE (US)

( * ) Notice: Subject to any disclaimer, the term of this patent is extended or adjusted under 35 U.S.C. 154(b) by 503 days.

(21) Appl. No.: 12/308,916

(22) PCT Filed: Jun. 29, 2007

(86) PCT No.: PCT/US2007/015181
§ 371 (c)(1),
(2), (4) Date: Dec. 29, 2008

(87) PCT Pub. No.: WO2008/005361
PCT Pub. Date: Jan. 10, 2008

(65) Prior Publication Data
US 2009/0319591 A1  Dec. 24, 2009

Related U.S. Application Data

(60) Provisional application No. 60/818,113, filed on Jun. 30, 2006.

(51) Int. Cl.
*G06F 19/00* (2011.01)
(52) U.S. Cl. ............................................ 702/19; 702/20
(58) Field of Classification Search ........................ None
See application file for complete search history.

(56) References Cited

U.S. PATENT DOCUMENTS

| | | | | |
|---|---|---|---|---|
| 6,312,911 | B1 * | 11/2001 | Bancroft et al. | 435/6.11 |
| 6,961,664 | B2 * | 11/2005 | Selifonov et al. | 702/19 |
| 7,204,425 | B2 * | 4/2007 | Mosher et al. | 235/492 |
| 7,913,924 | B2 * | 3/2011 | Silverbrook et al. | 235/494 |
| 2007/0061085 | A1 * | 3/2007 | Fernandez | 702/20 |

OTHER PUBLICATIONS

U.S. Appl. No. 60/818,113, filed Jun. 30, 2006.
Patent Cooperation Treaty Application No. PCT/US2007/015181 filed Jun. 29, 2007.
A Security System for Personal Genome Information at DNA Level, Portal, The Guide to Computing Literature, http://portal.acm.org/citation.cfm?id=793866, Nov. 28, 2008, one page.
Kawazoe, et al., A Security System for Personal Genome Information at DNA Level, Proceedings of the IEEE Computer Society Bioinformatics Conference, 2002, seven total pages.

* cited by examiner

*Primary Examiner* — Lori A Clow
(74) *Attorney, Agent, or Firm* — Craig R. Miles; CR Miles, P.C.

(57) ABSTRACT

A computer implemented method of generating an identification element including storing an amount of identifiable object data obtained as a linear sequence of data elements in the memory of a computer and which can be fragmented to produce a plurality of identifiable object data fragments each having a number of data elements which corresponds to one of a set of random numbers generated by a random number generator each of the identifiable object data fragments translated into a linear sequence of DNA data elements and embedded to generate an identification element.

23 Claims, 5 Drawing Sheets

ATCGTCGAGAGCTAATGACTGAGCAGATGTGAATTACAGATGACAGTAGCATGTAGGCAGTAGTCATGTACCCACCAATTGGA
CCATAAGCTAGTGAGAGCCATTGATGCTAGTAGCCGAGAATCTCTAGGCCAAATGACTGAATGGTGCCGAGATAGAATTTACC
AGTTCACGTACTAAAATTGCATAGTACAGT

FIG.6

ATCGTCGAGAGCTAATGACTGAGCAGATGTGAATTACAGATGACAGTAGCATGTAGGCAGTAG*TCATGTACCCACCA*ATTGGA
CCATAAGCTAGTGAGAGCCA*TTGATGCTAGT*AGCCGAGAATCTCTAGGCCAAATGACTGAATGGTGCCGAGATAGAAT*TTACC*
*AGTTCACGTACTAAAATTGCATAGT*ACAGT

FIG.7

```
                            SEQUENCE LISTING

<160> NUMBER OF SEQ ID NOS: 18

<210> SEQ ID NO 1
<211> LENGTH: 72
<212> TYPE: DNA
<213> ORGANISM: Unknown
<220> FEATURE:
<223> OTHER INFORMATION: exemplary sequence used to illustrate invention

<400> SEQUENCE: 1
atcgtcgaga gctaatgact gtgaattaca gatgacagta gcatgtaggc agtagctagt         60
gagagatctc ta                                                             72

<210> SEQ ID NO 2
<211> LENGTH: 20
<212> TYPE: DNA
<213> ORGANISM: unknown
<220> FEATURE:
<223> OTHER INFORMATION: exemplary sequence to illustrate invention

<400> SEQUENCE: 2
atcgtcgaga gctaatgact                                                     20

<210> SEQ ID NO 3
<211> LENGTH: 34
<212> TYPE: DNA
<213> ORGANISM: unknown
<220> FEATURE:
<223> OTHER INFORMATION: expemplary sequence to illustrate the invention

<400> SEQUENCE: 3
gtgaattaca gatgacagta gcatgtaggc agta                                     34
```

```
<210> SEQ ID NO 4
<211> LENGTH: 11
<212> TYPE: DNA
<213> ORGANISM: unknown
<220> FEATURE:
<223> OTHER INFORMATION: exemplary sequence to illustrate the invention

<400> SEQUENCE: 4
gctagtgaga g                                                          11

<210> SEQ ID NO 5
<211> LENGTH: 7
<212> TYPE: DNA
<213> ORGANISM: unknown
<220> FEATURE:
<223> OTHER INFORMATION: exemplary sequence to illustrate the invention

<400> SEQUENCE: 5 atctcta                                                                7

<210> SEQ ID NO 6
<211> LENGTH: 6
<212> TYPE: DNA
<213> ORGANISM: unknown
<220> FEATURE:
<223> OTHER INFORMATION: exemplary sequence to illustrate the invention

<400> SEQUENCE: 6 aaaatt                                                                 6

<210> SEQ ID NO 7
<211> LENGTH: 73
<212> TYPE: DNA
<213> ORGANISM: unknown
<220> FEATURE:
<223> OTHER INFORMATION: exemplary sequence to illustrate invention

<400> SEQUENCE: 7
gagcagatat tggaccataa tgctagtagc cgagatggtg ccgagataga atacggacga      60
tcgatgaata tca                                                        73

<210> SEQ ID NO 8
<211> LENGTH: 8
<212> TYPE: DNA
<213> ORGANISM: unknown
<220> FEATURE:
<223> OTHER INFORMATION: exemplary sequence to illustrate invention

<400> SEQUENCE: 8 gagcagat                                                               8

<210> SEQ ID NO 9
<211> LENGTH: 12
<212> TYPE: DNA
<213> ORGANISM: unknown
<220> FEATURE:
<223> OTHER INFORMATION: exemplary sequence to illustrate the invention

<400> SEQUENCE: 9
attggaccat aa                                                         12

<210> SEQ ID NO 10
<211> LENGTH: 15
<212> TYPE: DNA
<213> ORGANISM: unknown
<220> FEATURE:
```

```
<223> OTHER INFORMATION: exemplary sequence to illustrate the invention

<400> SEQUENCE: 10
tgctagtagc cgaga                                                          15

<210> SEQ ID NO 11
<211> LENGTH: 17
<212> TYPE: DNA
<213> ORGANISM: unknown
<220> FEATURE:
<223> OTHER INFORMATION: exemplary sequence to illustrate the invention

<400> SEQUENCE: 11
tggtgccgag atagaat                                                        17

<210> SEQ ID NO 12
<211> LENGTH: 6
<212> TYPE: DNA
<213> ORGANISM: unknown
<220> FEATURE:
<223> OTHER INFORMATION: exemplary sequence to illustrate the invention

<400> SEQUENCE: 12 tacagt                                                                     6

<210> SEQ ID NO 13
<211> LENGTH: 15
<212> TYPE: DNA
<213> ORGANISM: unknown
<220> FEATURE:
<223> OTHER INFORMATION: exemplary sequence to illustrate the invention

<400> SEQUENCE: 13
gtcatgtacc cacca                                                          15

<210> SEQ ID NO 14
<211> LENGTH: 7
<212> TYPE: DNA
<213> ORGANISM: unknown
<220> FEATURE:
<223> OTHER INFORMATION: exemplary sequence to illustrate the invention

<400> SEQUENCE: 14 ccattga                                                                    7

<210> SEQ ID NO 15
<211> LENGTH: 15
<212> TYPE: DNA
<213> ORGANISM: unknown
<220> FEATURE:
<223> OTHER INFORMATION: exemplary sequence to illustrate the invention

<400> SEQUENCE: 15
ggccaaatga ctgaa                                                          15

<210> SEQ ID NO 16
<211> LENGTH: 17
<212> TYPE: DNA
<213> ORGANISM: unknown
<220> FEATURE:
<223> OTHER INFORMATION: exemplary sequence to illustrate the invention

<400> SEQUENCE: 16
ttaccagttc acgtact                                                        17

<210> SEQ ID NO 17
```

```
<211> LENGTH: 6
<212> TYPE: DNA
<213> ORGANISM: unknown
<220> FEATURE:
<223> OTHER INFORMATION: exemplary sequence to illustrate the invention

<400> SEQUENCE: 17 gcatag                                                                      6

<210> SEQ ID NO 18
<211> LENGTH: 196
<212> TYPE: DNA
<213> ORGANISM: unknown
<220> FEATURE:
<223> OTHER INFORMATION: exemplary sequence to illustrate the invention

<400> SEQUENCE: 18
atcgtcgaga gctaatgact gagcagatgt gaattacaga tgacagtagc atgtaggcag         60
tagtcatgta cccaccaatt ggaccataag ctagtgagag ccattgatgc tagtagccga        120
gaatctctag gccaaatgac tgaatggtgc cgagatagaa tttaccagtt cacgtactaa        180
aattgcatag tacagt                                                        196
```

METHOD OF GENERATING AN IDENTIFICATION ELEMENT

This application is the United States National Stage of International Patent Corporation Treaty Patent Application No. PCT/US2007/015181, filed Jun. 29, 2007, which claims the benefit of U.S. Patent Application No. 60/818,113, filed Jun. 30, 2006, each hereby incorporated by reference in the entirety.

I. TECHNICAL FIELD

An embedded data DNA sequence security system which utilizes an embedded data DNA sequence to differentiate each of a plurality of identifiable objects.

II. BACKGROUND

Existing computer and internet security such as cryptographic processes, tokens, dongles, so-called "uncopyable media," passwords, and various executable software protection schemes fail to prevent identity fraud. Such methods are incapable of ensuring that the person or entity at each end of a transaction is who he says he is. At the center of the problem are those individuals who steal other persons' identities so as to perform fraud, pranks, vandalism, espionage and other illegitimate activities. Thus, a predominant security issue is identity authentication.

While authentication takes various forms, authentication of the individual is particularly desirable. That is authentication directed to verifying that the individual seeking a benefit or pursuing a transaction is in fact who that individual claims to be, and not an impersonator. This authentication relies on verification being performed at or above a predetermined minimum level of confidence.

Traditional methods of authenticating individuals have relied primarily on secret passwords, identification cards, photographic identification, or the like. Password-only authentication can be implemented entirely in software. However, password-only authentication has a number of disadvantages. For example, a password's viability is enhanced, among other ways, by increasing its length, by controlling its composition and by it being frequently changed. This, however, is cumbersome and, additionally, passwords can be lost or stolen, particularly written passwords. Passwords can be inadvertently disclosed to crackers via various ploys, such as observing the password's entry on a keyboard. Moreover, passwords can be intercepted as they are transported from the user to a desired computer server. Consequently, password-only authentication fails to provide adequate security. The shortcomings inherent with the conventional security measures have prompted an increasing interest in biometric security technology. That is, verifying a person's identity by personal biological characteristics, such as voice printing, finger printing, iris scans, or deoxyribonucleic acid ("DNA") sequence matching.

Surprisingly, even though numerous patents and patent applications include the term DNA as a biometric identifier (see for example U.S. patent application Ser. No. 6,871,287 which utilizes the term "DNA mapping" once but does not enable DNA mapping as a biometric to verify the identity of a person), it appears that a significant number of problems remain with respect to defining, obtaining and using DNA as a biometric identifier to verify the identity of a person.

A significant problem with using DNA as a biometric identifier can be that no attempt is made to cross-reference the user's alphanumeric identity data (i.e., name, address, Social Security number, etc.) against a database of identities which can determine, to a high degree of certainty, whether the alphanumeric identity data being offered with the biometric identity data is suspicious or subject to fraud. Without such cross-checking, a person submitting a biometric exemplar together with stolen alphanumeric identity data cannot be recognized as the fraud that he is by the anonymous computer systems which are so prevalent today.

Another significant problem with using DNA as a biometric identifier can be that no standardized region of the human genome has been identified which can be amplified using a limited set of DNA primers which generates an amplified DNA region of sufficiently high degree of variability among persons to allow identity verification with one-hundred percent certainty.

Another significant problem with using DNA as a biometric identifier can be that no method of personal identification includes a DNA as a biometric identifier to verify the familial connection to maternal relations with one hundred percent certainty.

Another significant problem with using DNA as a biometric identifier can be that no method of personal identification includes a DNA biometeric identifier which allows differentiation and identification of identical twins.

The inventive personal identity security system described herein addresses each of these problems.

III. DISCLOSURE OF INVENTION

Accordingly, a broad object of the invention can be to provide an identification element which can be generated in a sufficiently large number of permutations and combinations to allow a plurality of identifiable objects(s) to be differentiated. Additionally, the identification element can contain an amount of identifiable object data sufficient to verify identification of each member of the plurality of identifiable objects even when the plurality of identifiable objects contains two or more substantially identical members, as a non-limiting example, identical twins in a population.

Another broad object of the invention can be to provide an embedded data DNA sequence as a particular embodiment of the identification element which can be utilized in whole or in part to differentiate and verify identity as to each of a plurality of identifiable objects. As to certain embodiments of the invention the embedded data DNA sequence can be utilized as part of an embedded DNA sequence security system to verify identity of a person authorized to access an amount of data embedded in the embedded data DNA sequence or correspondingly matched to the embedded data DNA sequence or to the person whose identity can be verified with the embedded data DNA and stored in any of a numerous and varied remote databases which can contain without limitation health information, financial information, security information, or the like.

The term "identifiable object(s)" as used herein broadly encompasses any object including, without limitation, a person, an animal, a plant, or any isolated part or collection thereof such as an organ(s), a tissue(s), a cell(s) or cell line(s); a biological particle such as a virus, a bacteria, a clone, a prion, or any isolated part or collection thereof; an article of manufacture or any isolated part or collection thereof, or any other isolatable object or collection of objects whether tangible or intangible for which it may be desirable to associate an identifier for the purpose of differentiation.

The term "identifiable object data" as used herein broadly encompasses any manner of data relatable to the identifiable object which can be encoded by use of an algorithm to produce a linear sequence of data elements such as digital code and decoded by use of a corresponding algorithm to produce the original identifiable object data which can include without limitation "DNA sequence data" of a single gene or a plurality of genes, in part or in whole, obtained from a person, animal, organ, tissue, cell or cell line, bacteria, virus, or other biological particle containing DNA and specifically DNA regions of sufficiently high degree of variability to allow identity verification among a plurality of objects with substantially one-hundred percent certainty whether obtained from the identifiable object or another source and can be as to certain embodiments of the invention the genes which encode for ribosomal ribonucleic acids or mitochondrial ribonucleic acids; biometric data such as face recognition, fingerprints, hand geometry, iris recognition, voice dynamics, signature, keystroke dynamics, hand vein recognition, ear recognition, facial thermogram, palm prints, or like; parametric data such as the name, age, hair color, social security number, mother's maiden name, or the like; data relating to an article of manufacture without limitation the material, material dimensions, method of manufacture, method of use, or the like; health information; financial or credit card information; transaction information; image representations, document representations; DNA or RNA on magnetic strips of credit cards, ATM cards, and card based identification documents; or the like.

The term "embed" or "embedded" or "embedding" broadly encompasses generating one linear sequence of data elements from a plurality of identifiable object data fragments, as further described below. While typically each of the plurality of identifiable object fragments are oriented in the embedded sequence in the same reading direction as in the linear sequence of data elements from which the plurality of identifiable object data fragments was generated, one or more of the plurality of identifiable object fragments can be embedded in reverse of the original reading direction. Specifically, as to those embodiments of the invention which generate one linear sequence of DNA data elements from one or more than one plurality of DNA fragments with one or more of the DNA fragments established in the 3' to 5' orientation or one or more of the DNA fragments established in the 5' to 3' orientation random combination to generate one linear sequence of DNA elements (A, G, C, T in combinations and permutations which represent the primary structure of DNA molecules or are utilized to encode other identifiable object data as further discussed below).

The term "embedded DNA sequence" broadly encompasses any DNA sequence generated by "embedding" one or more than one plurality of DNA fragments regardless as to whether any plurality of DNA fragments is generated by fragmenting an amount of DNA sequence representing the primary structure of a DNA molecule in whole or in part by or fragmenting a linear sequence of data elements corresponding to an amount of identifiable object data whether biometric data, parametric data, or other manner of data and translating such plurality of identifiable object data fragments (or translating the a linear sequence of data elements corresponding to an amount of identifiable object data prior to translation) to generate a plurality of DNA fragments.

Naturally, further objects of the invention are disclosed throughout other areas of the specification, drawings, photographs, and claims.

V. MODE(S) FOR CARRYING OUT THE INVENTION

According to various embodiments of the invention, the shortcomings of conventional information security systems are addressed by providing a computer-based embedded data DNA sequence security system and methods of making and using embedded data DNA sequences and embedded data DNA sequence security systems.

The present inventive embedded data DNA sequence security system may be described herein in terms of functional block components, screen shots, optional selections and various process steps. It should be appreciated that such functional blocks may be realized by any number of hardware or software components configured to perform the specified functions. For example, the present invention may employ various integrated circuit components which function without limitation as memory elements, processing elements, logic elements, look-up tables, or the like, which may carry out a variety of functions under the control of one or more microprocessors or other control devices.

Similarly, the software elements of the present invention may be implemented with any programming or scripting language such as C, C++, JAVA, COBOL, PERL, or any graphical user interface programming language, extensible markup language (XML), Microsoft's VISUAL STUDIO.NET, VISUAL BASIC, or the like, with the various algorithms or Boolean Logic being implemented with any combination of data structures, objects, processes, routines or other programming elements. Further, it should be noted that the present invention might employ any number of conventional techniques for data transmission, signaling, data processing, network control, and the like.

It should be appreciated that the particular implementations shown and described herein are illustrative of the invention and its best mode and are not intended to otherwise limit the scope of the present invention in any way. Indeed, for the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical electronic security system.

As will be appreciated by one of ordinary skill in the art, the present invention may be embodied as a method, a data processing system, a device for data processing, a computer program product, or the like. Accordingly, the present invention may take the form of an entirely software embodiment, an entirely hardware embodiment, or an embodiment combining aspects of both software and hardware. Furthermore, the present invention may take the form of a computer program product on a computer-readable storage medium having computer-readable program code means embodied in the storage medium. Any suitable computer-readable storage medium may be utilized, including hard disks, CD-ROM, optical storage devices, magnetic storage devices, ROM, flash RAM, or the like.

The present invention may be described herein with reference to screen shots, block diagrams and flowchart illustrations of the embedded data DNA sequence security system or embedded data DNA sequence security computer programs, applications, or modules which can be utilized separately or in combination with such embedded data DNA sequence security system in accordance with various aspects or embodiments of the invention. It will be understood that each functional block of the block diagrams and the flowchart illustrations, and combinations of functional blocks in the block diagrams and flowchart illustrations, respectively, can be implemented by computer program instructions. These computer program instructions may be loaded onto a general purpose computer, special purpose computer or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware based computer systems which perform the specified functions or steps, or suitable combinations of special purpose hardware and computer instructions.

Figure 1:
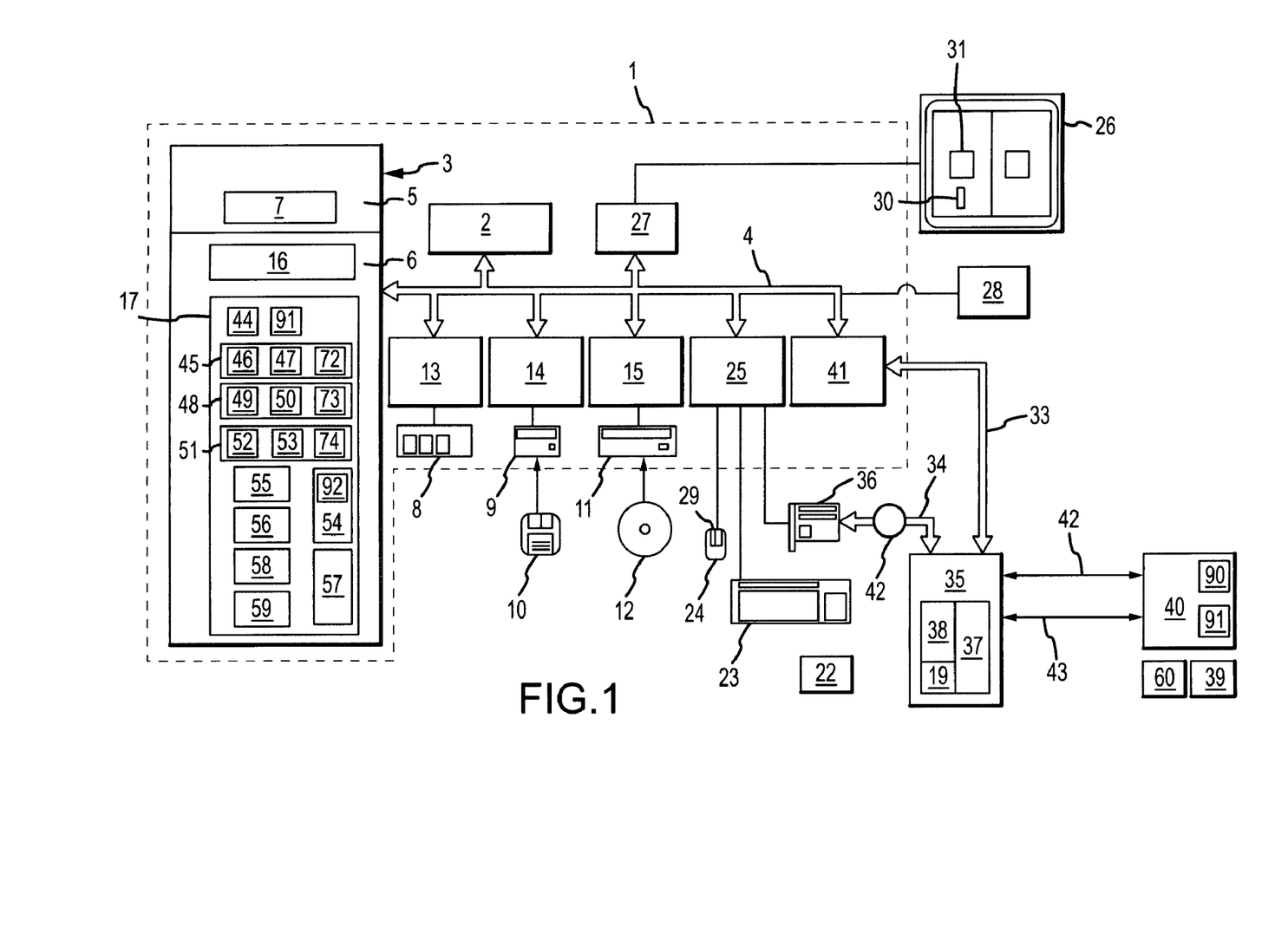
FIG. 1 provides a block diagram of the hardware and software components of a particular embodiment of the inventive embedded data DNA sequence security system.

Now referring primarily to FIG. 1, which shows a block diagram of a non-limiting embodiment of a computer which can be utilized to implement embodiments of the embedded data DNA sequence security system including, without limitation, a server computer (1) having at least one processing unit (2), a memory element (3), and a bus (4) which operably couples components of the computer (1), including, without limitation the memory element (3) to the processing unit (2). The server computer (1) may be a conventional computer, a distributed computer, or any other type of computer; the invention is not so limited. The processing unit (2) can comprise without limitation one central-processing unit (CPU), or a plurality of processing units which operate in parallel to process digital information, or a digital signal processor (DSP) plus a host processor, or the like. The bus (4) can be without limitation any of several types of bus configurations such as a memory bus or memory controller, a peripheral bus, and a local bus using any of a variety of bus architectures. The memory element (3) can without limitation be a read only memory (ROM) (5) or a random access memory (RAM) (6), or both. A basic input/output system (BIOS) (7), containing routines that assist transfer of data between the components of the computer (1), for example during start-up, can be stored in ROM (5). The computer (1) can further include a hard disk drive (8) for reading from and writing to a hard disk (not shown) a magnetic disk drive (9) for reading from or writing to a removable magnetic disk (10), and an optical disk drive (11) for reading from or writing to a removable optical disk (12) such as a CD ROM or other optical media.

The hard disk drive (8), magnetic disk drive (9), and optical disk drive (10) are connected to the bus (4) by a hard disk drive interface (13), a magnetic disk drive interface (14), and an optical disk drive interface (15), respectively. The drives and their associated computer-readable media provide non-volatile storage of computer-readable instructions, data structures, program modules and other data for the server computer (1). It can be appreciated by those skilled in the art that any type of computer-readable media that can store data that is accessible by a computer, such as magnetic cassettes, flash memory cards, digital video disks, Bernoulli cartridges, random access memories (RAMs), read only memories (ROMs), and the like, may be used in the exemplary operating environment.

The computer (1) can further include an operating system (16) and an embedded data DNA sequence security application (17). The particular non-limiting embodiment of the embedded data DNA sequence security application (17) as shown in the Figure and described below includes application modules that provide: a random number generator (44), a DNA sequence buffer (45), a DNA sequence generator (46), a DNA sequence fragment generator (47), a parametric sequence buffer (48), a parametric sequence generator (49), a parametric sequence fragment generator (50), a biometric sequence buffer (51), a biometric sequence generator (52), a biometric sequence fragment generator (53), a sequence translator (54), an embedded sequence generator (55), a sequence compressor-decompressor (56), an embedded sequence buffer (57), a vector configuration generator (58), and a sequence counter (59), each described in greater detail below, may be stored on or in the hard disk, magnetic disk (10), optical disk (12), ROM (5), in RAM (6) as shown by the particular embodiment of FIG. 1, or alternately the functionalities of the embedded data DNA sequence application (17)

may be implemented as an application specific integrated chip (ASIC) or file programmable gate array (FPGA), or the like.

A computer user (22) can enter commands and information into the server computer (1) through input devices such as a keyboard (23) and pointing device such as a mouse (24). Other input devices (not shown) may include a microphone, joystick, game pad, satellite dish, scanner, magnetic strip of a credit card, ATM card, or other form of identity card, or the like. These and other input devices are often connected to the processing unit (2) through a serial port interface (25) that can be coupled to the bus (4), but may be connected by other interfaces, such as a parallel port, game port, or a universal serial bus (USB). A monitor (26) or other type of display device can also be connected to the bus (4) via interfaces such as a video adapter (27), or the like. In addition to the monitor (24), the server computer (1) can further include other peripheral output devices (28), such as speakers and printers.

A "click event" occurs when the computer user (22) operates at least one function of the embedded data DNA sequence security application (17), or other program or other application function, through the use of a command which for example can include pressing or releasing the left mouse button (29) while a pointer (30) is located over a control icon (31) displayed on the monitor (26). However, it is not intended that a "click event" be limited to the press and release of the left button (29) on a mouse (24) while a pointer (30) is located over a control icon (31). Rather, the term "click event" is intend to broadly encompass a command by the computer user (22) through which a function of the operating system (16) or an application such as the embedded data DNA sequence security application (17) is activated or performed, whether through clickable selection of one or a plurality of control icon(s) (31) or by computer user (22) voice command, keyboard stroke(s), mouse button, touch screen, or otherwise. It is further intended that control icons (31) can be configured without limitation as a point, a circle, a triangle, a square (or other geometric configurations or combinations or permutations thereof), or as a check box, a drop down list or other index containing a plurality of identifiers, an information field which can contain or which allows input of a string of alphanumeric characters such as a street address, zip code, county code, or natural area code, or by inputting a latitude/longitude or projected coordinate X and Y, or other notation, script, character, or the like.

The server computer (1) may operate in a networked environment using logical connections (33)(34) to one or a plurality of remote server computers (35). These logical connections (33)(34) are achieved by a communication device (36) (41) coupled to or a part of the server computer (1); the invention is not limited to a particular type of communications device (36)(41). Each remote server computer (35) can include a part or all of the elements above-described as included in the server computer (1) although only a single box has been illustrated in FIG. 1 for the remote server computer (35). The remote server computer (35) can provide a searchable database (37) in which embedded data DNA sequences (38) of clients (39) can be retrievably stored. The logical connections (33)(34) depicted in FIG. 1 can establish a local-area network (LAN) or a wide-area network (WAN). Such networking environments are commonplace in offices, enterprise-wide computer networks, intranets and the Internet (42). Similarly, each of the plurality of remote server computers (35) can operate in the networked environment using similar logical connections (42)(43) to communicate with one or a plurality of client computers (40). Each client computer (40) can include a part or all of the elements described herein for the server computer (1).

When used in a LAN-networking environment, the server computer (1) can be connected to the local network (33) through a network interface or adapter, which is one type of communications device (41). When used in a WAN-networking environment, the server computer (1) typically includes a modem (36), a type of communications device, or any other type of communications device for establishing communications over the wide area network, such as the Internet (42). The modem (36), which may be internal or external, is connected to the bus (4) via the serial port interface (25). In a networked environment, the embedded data DNA sequence security application (17), or portions thereof, may be stored in the remote server computer (35) or in the client computer (40). It is appreciated that the logical connections (33)(34) (42)(43) shown are exemplary and other hardware means and communications means for establishing a communications link between the server computer (1) and one or a plurality of remote server computers (35) and between each one of the plurality of remote server computers (35) and each of a plurality of client computers (40) can be utilized.

While the computer means and the network means shown in FIG. 1 can be utilized to practice preferred embodiments of the invention including the best mode, it is not intended that the description of the best mode of the invention or any preferred embodiment of the invention be limiting with respect to the utilization of a wide variety of similar, different, or equivalent computer means or network means to practice embodiments of the invention which include without limitation hand-held devices, such as personal digital assistants or camera/cell phone, multiprocessor systems, microprocessor-based or programmable consumer electronics, network PCs, minicomputers, mainframe computers, PLCs, or the like.

Now referring primarily to FIGS. 1-7, a particular method of generating an identification element (19) (see FIG. 1) and specifically an embedded data DNA sequence (38) (see FIGS. 1, 6 and 7) which can be utilized for identification, authentication, verification, or differentiation of each of a plurality of identifiable objects (60), as above described is shown. While a particular method of producing an identification element (19) or an embedded data DNA sequence (38) is shown and described as a plurality of consecutive steps, it is not intended that the steps to make and use embodiments of the invention be performed in the consecutive order shown and described. Rather, the particular method of generating an identification element (19) or an embedded data DNA sequence (38) as shown and described is intended to provide an example of how to make and use certain elements and functions of the invention which can be ordered in numerous and varied ways whether in serial or in parallel to generate the embedded data DNA sequence (38) or the identification element (19) utilizing a fewer or greater steps whether in the same or different order than those shown or described to generate an embedded data DNA sequence (38).

Figure 2:
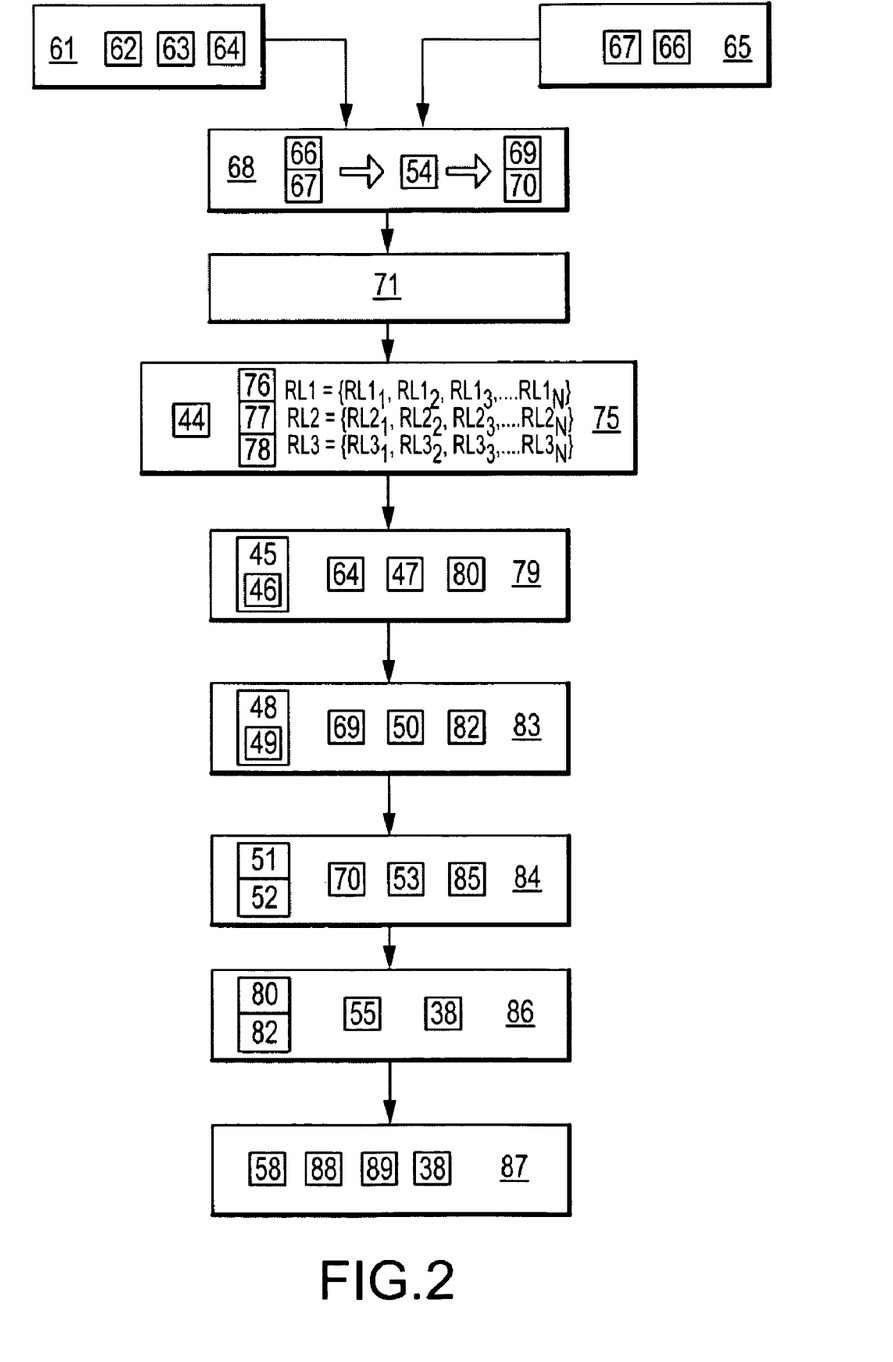
FIG. 2 provides a block diagram which shows a particular method of producing an embodiment of the inventive embedded data DNA sequences.

Now referring primarily to FIG. 2, in a first step (61), a cell sample (62) (the term "cell sample" broadly encompassing any sample regardless of the source (for example, human, animal, plant, bacteria, virus, or the like) which can be manipulated by one or more procedures to yield an amount of DNA sequence data (64) (also referred to as DNA sequence data) represented by a linear sequence of DNA data elements including A, G, C, and T in various permutations and combinations to encode each of Adenosine, Guanine, Cytosine, and Thymine. As to certain example of a non-limiting embodiment of the invention the cell sample (62) can be obtained from a person (63) by performing a buccal swab which engages a cotton swab with the cheek inside the mouth of the donor (63). The buccal swab collects epithelial cells off the cheek inside the mouth of the person (63). Because all nucleated cells of a person (63) have the same DNA, the epithelial cells collected on the swab will contain DNA suitable use in the method of producing of embedded data DNA sequence (38). However, it is not intended that the invention be limited to collection of the cell sample (62) by a buccal swab. Rather it is to be understood that the cell sample (62) can be obtained from the person (63) (or animal, plant, cell, clone, bacteria, or other DNA containing particle) through a variety of procedures all of which may suitable for processing to obtain an amount of DNA sequence data (64).

One manner of obtaining an amount of DNA sequence data (64) can be to amplify target regions of DNA isolated from the cell sample (62) using polymerase chain reaction ("PCR"). See for example, White, Bruce A., ed. *PCR Cloning Protocols: From Molecular Cloning to Genetic Engineering. Methods in Molecular Biology*, Volume 67. Totowa: Humana Press Inc (1997), hereby incorporated by reference herein. The target regions of the DNA to be amplified can be selected by utilizing short DNA oligonucleotide primers that are complimentary to and anneal with the DNA sequences flanking the genes which encode ribosomal ribonucleic acids ("rRNAs") or other genes or regions of the chromosome which separately or in combination can provide sufficient variability as above-described. PCR allows extension of the annealed primers to include about eight kilobases of the target region of the DNA.

rRNAs contain regions in which the primary sequence can be highly variable as well as short regions of primary sequence which is universally conserved. These highly variable regions of the amplified rRNA coding regions of chromosomal and mitochondrial DNA (or other DNA sequences having a similar level of sequence variability) can be utilized in the production of embedded data DNA sequence (38) or other identification elements (19).

The DNA sequence data (64) of the amplified target regions of the DNA obtained from the person (63) can be analyzed utilizing the chain-termination method developed by Frederick Sanger and coworkers in 1975. See *DNA Sequencing With Chain-Terminating Inhibitors*, Proc. Natl. Acad. Sci. 74(12): 5463-5467 (1977), hereby incorporated by reference herein. However, it is to be understood that any manner of obtaining an amount of DNA sequence data (64) of the DNA target regions can be utilized to provide the amount of DNA sequence data (64) for use in the production of embedded data DNA sequence (38) or other identification element (19). As to certain embodiments of the invention, the DNA sequence data (64) obtained can be stored in the memory element (72) of the DNA sequence buffer (45) and can be retrieved by operation of the DNA sequence generator (46).

Certain embodiments of the invention can utilize the DNA sequence data (64) corresponding to variable regions of rRNA genes for the production of embedded data DNA sequence (38) or identification elements (19). An advantage of utilizing rRNA genes for the production of identification elements (19) or embedded data DNA sequence (38) can be that the variable regions of the rRNA genes exhibit a high degree of base pairing important in secondary and tertiary conformers of the rRNA molecule. As such, when two bases in the same rRNA molecule are involved in base pairing or higher order secondary or tertiary interactions, a base substitution at one position involved in the interaction can be indicative of necessary corresponding substitutions at other positions in the molecule. Analysis of these base substitutions and the corresponding substitutions at remote locations in genes which encode for the rRNA can provide a unique tool for identifying the person (63). Additionally, an amount of DNA sequence data (64) when obtained from a mitochondrial DNA can provide a maternal identifier sequence which can be used to establish a level of familial relatedness between the person (63) and other persons similar to the use of the "mother's maiden name" as a personal identifier except that the maternal identifier sequence will be entirely unique to the person.

In a second step (65), biometric data (66) such as face recognition, fingerprints, hand geometry, iris recognition, voice dynamics, signature, keystroke dynamics, hand vein recognition, ear recognition, facial thermogram, palm prints, or the like, can be utilized in the production of embedded data DNA sequence (38) or other identification elements (19). As to certain embodiments of the invention, the biometric data (66) obtained can be stored in the memory element (74) of the biometric sequence buffer (51) and can be retrieved by operation the biometric sequence generator (51).

Similarly, as to other embodiments of the invention relating to the differentiation, identification, authentication, or verification of any of the plurality of identifiable objects (60) which cannot yield DNA from a biological source or biometric data from a biological entity (such as articles of manufacture, documents, or the like) parametric data (67) only can be obtained which can be utilized in the production of embedded data DNA sequence, even as to those embodiments of invention in which the first step (61) is not incorporated or where no DNA sequence is obtained from a cell sample (62). As to certain embodiments of the invention, the parametric data (67) obtained can be stored in the memory element (73) of the parametric sequence buffer (48) and can be retrieved by operation of the parametric sequence generator (49).

As but one example of biometric data (66) which can be obtained in the second step (65), a linear array of sites on the amplified DNA can be recognized and cleaved by specific restriction endonucleases to generate a set of DNA fragments that contain the highly variable regions of the amplified DNA unique to the identified person (63). The set of DNA fragments containing the unique variable regions can be separated by electrophoresis in an agarose gel to generate a DNA fragment pattern (DNA fingerprint) unique to the person (63) which can be visualized under UV illumination and images of the pattern produced by photographic or digital means. The DNA fingerprint can be used to identify the person (63) with a certainty on the order of 99.9% even in the case when the person (63) is one of identical twins.

As to certain embodiments of the invention, only one of: the DNA sequence generator (46), the parametric sequence generator (49), or the biometric sequence generator (52) may be provided along with the corresponding function, or alternately the respective functions of these plurality of sequence generators may be combined into a single sequence generator. Additionally, certain embodiments of the invention may include each one of: the DNA sequence generator (46), the parametric sequence generator (49), or the biometric sequence generator (52) but only one may be utilized depending on the particular application. Moreover, as to certain embodiments of the invention, the order in which the DNA sequence generator (46), parametric sequence generator (49), biometric sequence generator (52) are activated or function may vary depending upon the application. To broadly describe each of these alternate embodiments of the invention in generic fashion, these components may also be referred to as: a first linear sequence generator, a second linear sequence generator, and a third linear sequence generator each of which can function in serial or in parallel can correspondingly generate a first linear sequence of data elements, a second linear sequence of data elements, and a third linear sequence of data elements corresponding to a first amount of identifiable object data, a second amount of identifiable object data, and a third amount of identifiable object data, and so forth.

In a third step (68), a sequence translator (54) of the embedded DNA sequence security application (17) can function to encode each of the first linear sequence of data elements, the second linear sequence of data elements, or the third linear sequence of data elements into a corresponding linear sequence utilizing the characters A, G, C, and T in combinations or permutations which can be decoded to generate the original linear sequence of data elements. For example, in the embodiment of the invention shown by FIGS. 1 and 2, a sequence translator (54) can translate an amount of parametric data (67) and an amount of biometric data (66) to a corresponding amount of parametric data sequence (69) and amount of biometric data sequence (70) each including the characters A, G, C, and T in serial linear combinations or permutations which can be decoded to generate the original amount of parametric data (67) or the original amount of biometric data (66). The DNA sequence data (64) from biological sources being already obtained in the prior first step (61).

In a fourth step (71), the DNA sequence data (64) and the parametric data sequence (69) and the biometric data sequence (70) are each separately stored into the respective memory elements (72)(73)(74) of the DNA sequence buffer (45), the parametric sequence buffer (48), and the biometric sequence buffer (51) of the embedded data DNA sequence security application (17).

In a fifth step (75), the random number generator (44) of the embedded data DNA sequence security application (17) generated sets of random numbers such as a first set of random numbers (RL1=$RL1_1$, $RL1_2$) (76), a second set of random numbers (RL2=$RL2_1$, $RL2_2$ ...) (77), and a third set of random numbers (RL3=$RL3_1$, $RK3_2$ ...) (greater or fewer The random number generator (44) can utilize any algorithm which generates a sufficient degree of randomness in the sets of random numbers (76)(77)(78). As but one example without limitation, the random number generator (44) can be a CryptGenRandom random number generator function included in Microsoft Coporation's Cyptographic Application Programming Interface, or similar random generator function. As to a particular embodiment of the invention, the random number generator (44) generates the first set of random numbers (76) which can be utilized by the DNA sequence buffer (45) and the second set of random numbers (77) which can be utilized by the parametic sequence buffer (48) or the biomentric sequence buffer (51) as further described below. In a second embodiment of the invention, the random number generator (44) can further generate a third set of random numbers (78) utilized by either the parametic sequence buffer (48) or the biometric sequence buffer (51).

Figure 3:
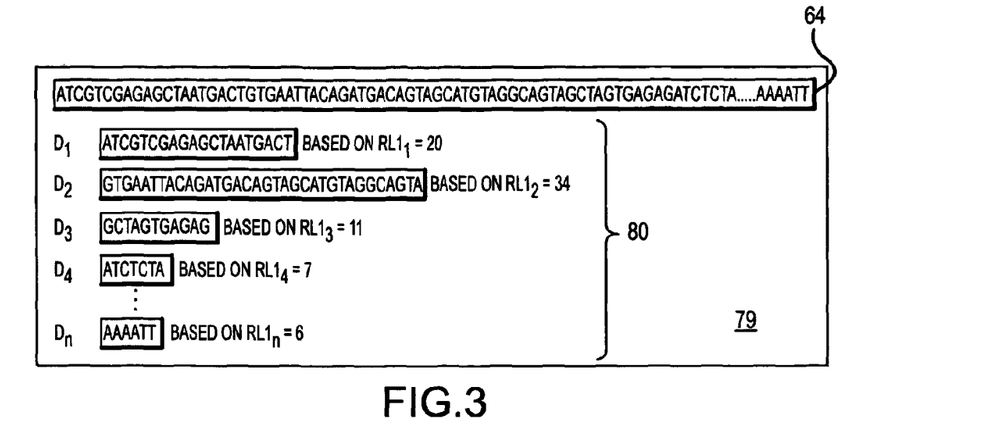
FIG. 3 provides a block diagram which shows a particular method of fragmenting an exemplary DNA sequence (SEQ. ID. NO.:1) to produce an exemplary set of DNA sequence fragments (SEQ. ID NO:2; SEQ. ID NO:3; SEQ. ID NO:4; SEQ. ID NO:5; SEQ. ID NO:6).

Now referring primarily to FIGS. 1, 2, and 3, in a sixth step (79), the DNA sequence generator (46) of the DNA sequence buffer (45) (or the first linear sequence generator) functions to retrieve the DNA sequence data (64) prior stored corresponding to the cell sample (62) obtained from the person (63). The DNA sequence fragment generator (47) of the DNA sequence buffer (45) (or the first sequence fragment generator) can function to fragment the DNA sequence(s) (64) to establish a plurality of DNA sequence fragments (80) (or first plurality of DNA sequence fragments) based upon the first set of random numbers (76). As shown in FIG. 3, the first set of random numbers (RL1=$RL1_1$, $RL1_2$ ...) (76) can be applied to the DNA sequence data (64) such that where $RL1_1$=20 the first 20 consecutive positions of the DNA sequence data (64) are isolated as a first DNA fragment (D1). Where $RL1_2$=34 the next 34 consecutive positions of the DNA sequence data (64) are isolated as the second DNA fragment (D2), and so forth.

Figure 4:
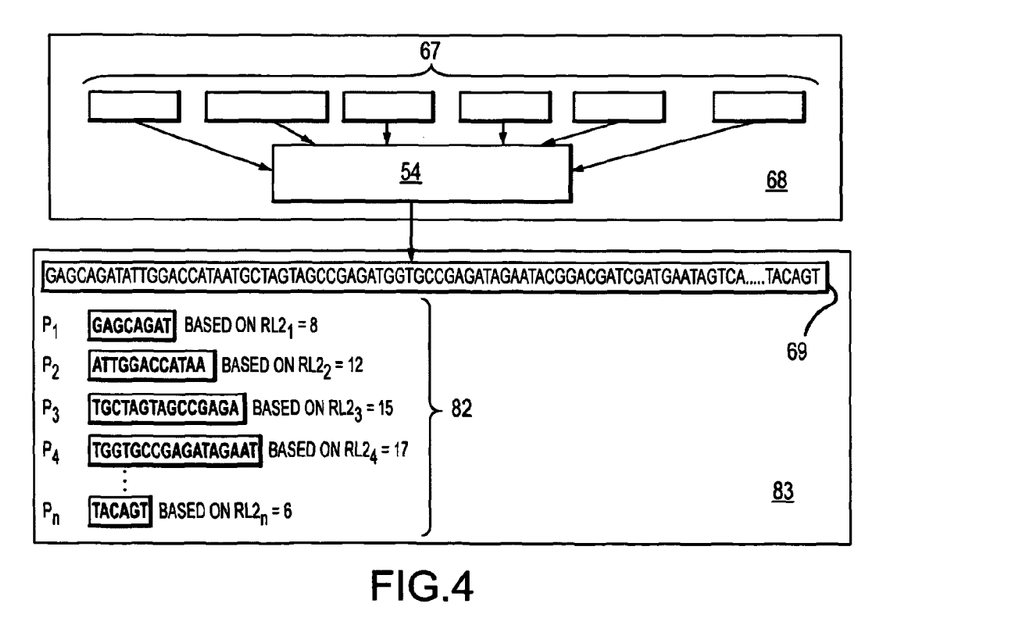
FIG. 4 provides a block diagram which shows a particular method of fragmenting an exemplary DNA sequence (SEQ. ID NO. 7) to produce an exemplary set of DNA sequence fragments SEQ. ID NO:8; SEQ. ID NO:9; SEQ. ID NO:10; SEQ. ID NO: 11; SEQ. ID NO:12).

Now referring primarily to FIGS. 1, 2 and 4, in a seventh step (83) the parametric sequence generator (49) of the parametric sequence buffer (48) (or the second linear sequence generator) can function to retrieve the parametric data sequence (69) which corresponds to the person (63) or the identifiable object (60). The parametric sequence fragment generator (50) of the parametric sequence buffer (48) (or second sequence fragment generator) can function to fragment the parametric data sequence (69) into a plurality of parametric data sequence fragments (82) (or second plurality of DNA sequence fragments) based on the second set of random numbers (77). As shown in FIG. 4, the second set of random numbers (RL2=$RL2_1$, $RL2_2$ ...) (77) can be applied to the parametric data sequence (69) such that where $RL21_1$=8 the first 8 consecutive positions of the parametric data sequence (69) are isolated as a first parametric data sequence fragment (P1). Where $RL2_2$=12 the next 12 consecutive positions of the parametric data sequence (69) are isolated as the second parametric data sequence fragment (P2), and so forth.

Figure 5:
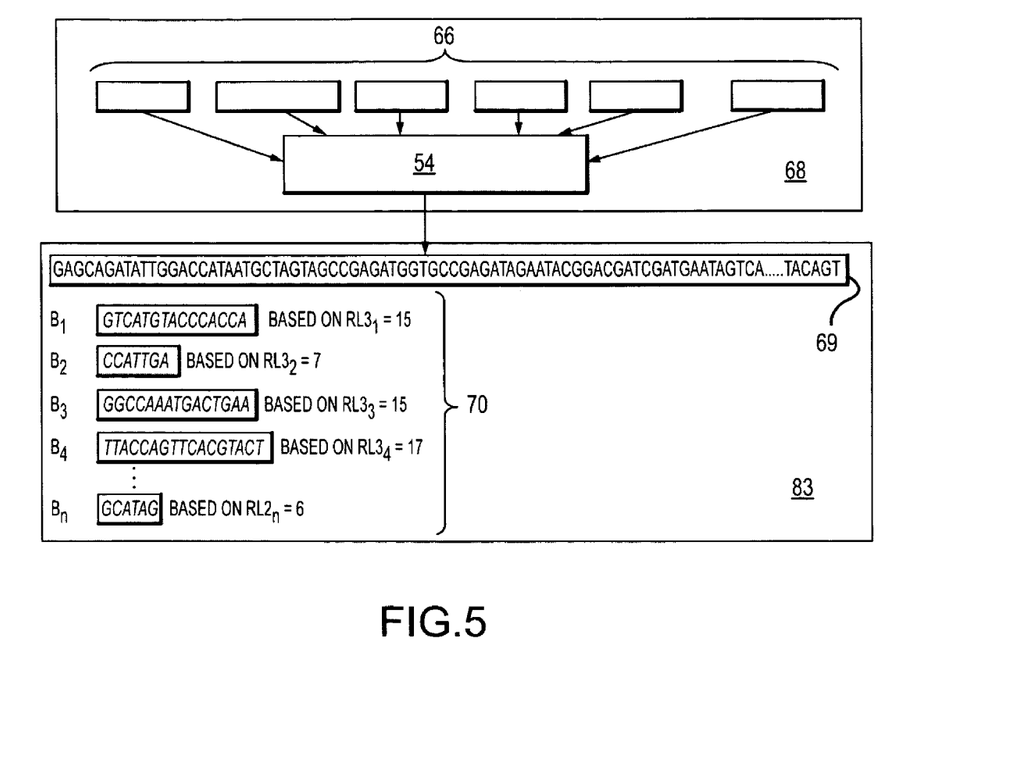
FIG. 5 provides a block diagram which shows a particular method of fragmenting an exemplary DNA sequence (SEQ. ID NO.:7) to produce an exemplary set of DNA sequence fragments SEQ. ID NO:13; SEQ. ID NO:14; SEQ. ID NO:15; SEQ. ID NO:16; SEQ. ID NO:17).
Figure 6:
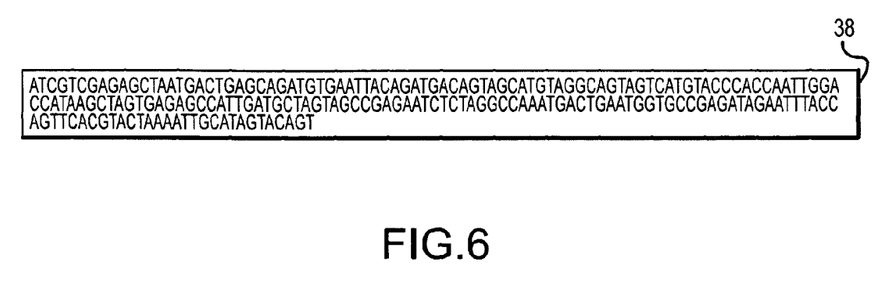
FIG. 6 provides an example of an embedded data DNA sequence (SEQ. ID NO.: 18) which can be utilized as an identification element of an identifiable object.
Figure 7:
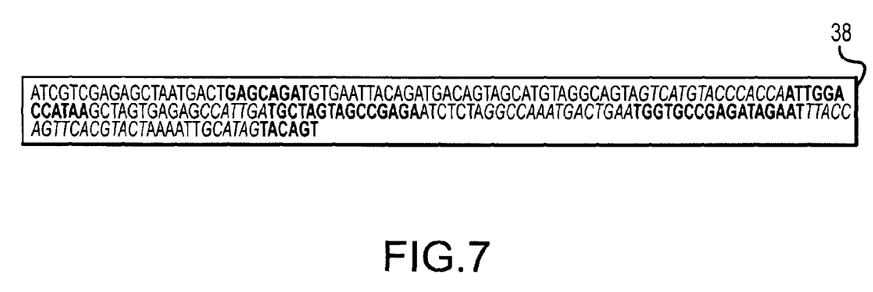
FIG. 7 provides the example of the embedded data DNA sequence (SEQ. ID NO. 18) shown in FIG. 6 indicating the DNA sequence fragments generated in FIG. 3 in regular type font, the DNA sequence fragments generated in FIG. 4 set out in bold type font, and the DNA sequence fragments generated in FIG. 5 in italics.

Now referring primarily to FIGS. 1, 2, and 5, in an eighth step (84) the biometric sequence generator (52) of the parametric sequence buffer (51) (or third linear sequence generator) can function to retrieve the biometric data sequence (70) which corresponds to the person (63). The biometric sequence fragment generator (53) of the biometric sequence buffer (51) (or third sequence fragment generator) can function to fragment the biometric data sequence (70) into a plurality of parametric data sequence fragments (85) (or third plurality of DNA fragments) based on the third set of random numbers (78). As shown in FIG. 5, the third set of random numbers (RL3=$RL3_1$, $RL3_2$ ...) (78) can be applied to the biometric data sequence (70) such that where $RL3_1$=15 the first 15 consecutive positions of the biometric data sequence (70) are isolated as a first biometric data sequence fragment (B1). Where $RL3_2$=7 the next 7 consecutive positions of the biometric data sequence (70) are isolated as the second biometric data sequence fragment (B2), and so forth.

Now referring primarily to FIGS. 1, 2, 6 and 7, in a ninth step (86) an embedded sequence generator (55) can function to generate an identification element (19) by generating one linear sequence of data elements from a plurality of identifiable object data fragments assembled or coupled end to end in random order. While typically each of the plurality of identifiable object fragments are oriented in the embedded sequence in the same reading direction as in the linear sequence of data elements from which the plurality of identifiable object data fragments was generated, one or more of the plurality of identifiable object fragments can be embedded in reverse of the original reading direction.

Specifically, as to those embodiments of the invention which include a sequence translator (54) the embedded sequence generator (55) can function to generate one linear sequence of DNA data elements from a first plurality of DNA fragments by random combination end to end typically with the DNA fragments established in the 3' to 5' reading direction in random combination; however, this does not preclude one or more of the DNA fragments being established in the 5' to 3' reading direction in the random combination, to generate one linear sequence of DNA data elements. In an alternate embodiment, the embedded sequence generator (55) can function to generate an embedded data DNA sequence (38) having a singular sequence of DNA sequence data elements from more than one plurality of DNA fragments (such as first plurality and a second plurality of DNA fragments or a first plurality, a second plurality and a third plurality of DNA fragments) by coupling the first plurality of DNA sequence fragments, the second plurality of DNA sequence fragments, the third plurality of DNA sequence fragments (if a third plurality of DNA sequence fragments are generated) by random combination end to end with one or more DNA fragments established in the 3' to 5' reading direction. Again, this does not preclude a 5' to 3' reading direction with regard to a part of the embedded data DNA sequence (38). The embedding process can function to intercalate an amount of DNA sequence data (64) obtained from biological sources such as a person (63) with an amount of DNA sequence data (64) obtained by translating an amount of identifiable object data such as an amount of parametric data (67) or an amount of biometric data (66). Various commercially available string insertion, deletion, and extraction algorithms can be modified to perform the functions of the encoding and decoding functions to embed an amount of DNA sequence data (64), biometric data sequence (70), parametric data sequence data (69) into a linear sequence of DNA elements.

Now referring primarily to FIGS. 1 and 2, in a tenth step (87), a vector configuration generator (58) can function along with the sequence translator (54) to configure dynamic values (88) (values which can change) such as time, date, geographic coordinates of the person (63), or the like, as vector data sequences (89) and embed one or a plurality vector data sequence(s) (89) as part of the embedded data DNA sequence (38).

Now referring primarily to FIG. 1, the inventive embedded data DNA sequence security application (17) can further include a sequence compressor-decompressor (56) which utilizes an algorithm to store the embedded data DNA sequence (38) utilizing less space in the memory elements (72)(73)(74) or other similar memory element.

Again referring primarily to FIG. 1, the inventive embedded data DNA sequence security application (17) can further include an embedded sequence buffer (57) which functions to provide temporary storage of the embedded data DNA sequence(s) (38), sequence compressor-decompressor (56), and the embedded sequence generator (55). In addition, the embedded sequence buffer (57) can further function to validate the embedded data DNA sequence (38). In this regard, the embedded sequence buffer (57) can include data communication error recognition algorithms such as cyclic redundancy checksum, frame checksum or Forward Error Correction and can further function to compare embedded DNA sequence(s) (38) against invalid DNA sequences. As but one non-limiting example, if the received DNA sequence received contained all A's, T's, C's or G's (for example, the DNA Sequence={AAAAAAAA . . . A}) such DNA sequences would be considered invalid DNA sequences.

Again referring primarily to FIG. 1, the inventive embedded data DNA sequence security application (17) can further include a sequence counter (59) which can function to track all statistics and counters during generation of the embedded data DNA sequence(s) (38).

Again referring primarily to FIG. 1, the inventive embedded data DNA sequence security application (17) can function to allow a client (39) which may be a patient requiring access to medical information from a remote location by utilization of one of a plurality of client computers (40). The server computer (1) can serve a graphic user interface module (91) to each one of the plurality of client computers (40) through the WAN utilizing the Internet (42) which can function by operation of the client computer (40) to generate a graphic user interface (90) which allows the client (39) to enter by click event either manually or from diskette (10), computer disk (12) or other memory, or by obtaining DNA sequence data (64) by DNA sequence analysis as above-described of a cell sample (62) obtained from the client (39), or other data entry method or combination of data entry methods, the embedded data DNA sequence (whether in whole or in part) into the client computer (40) to identify the client (39). Identification of the client (39) can authorize client (39) access to one or more of the plurality of remote server computers (35) and retrieve data such as medical records correspondingly matched to the embedded data DNA sequence in the searchable database (37) of the remote server computer (35) or to have the embedded DNA sequence decoder (92) function to decode portions of the embedded data DNA sequence (38) to retrieve and display in whole or in part DNA sequence data (64), biometric data (66) or parametric data (67).

Understandably, the embedded data DNA sequence (38) can be used in a variety of applications to allow identification of the client (39) to provide access to a numerous and wide variety of searchable databases (37) of a correspondingly numerous and wide variety of remote server computers (37) used to store as examples without limitation: health information, security information, financial and credit card information, terrorist information, manufacturing and product information.

As can be easily understood from the foregoing, the basic concepts of the present invention may be embodied in a variety of ways. The invention involves numerous and varied embodiments of an embedded data DNA sequence security system and methods of making and using embedded data DNA sequences and embedded data DNA sequence security systems As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of an "embedded sequence generator" should be understood to encompass disclosure of the act of "generating an embedded sequence" whether explicitly discussed or not and, conversely, were there effectively disclosure of the act of "generating an embedded sequence", such a disclosure should be understood to encompass disclosure of an "embedded sequence generator" and even a "means for generating an embedded sequence." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Thus, the applicant(s) should be understood to claim at least: i) each of the embedded data DNA sequence security systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof or to obtain any benefit of reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

In addition, the claims set forth below are intended describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A computer implemented method of generating an identification element, comprising:
   a) storing an amount of identifiable object data as a linear sequence of data elements in a memory element of a computer;
   b) generating a first set of random numbers utilizing a random number generator module, each random number of said first set of random numbers having a numeric value;
   c) applying said numeric value of each said random number generated to said linear sequence of data elements to establish a number of data elements in each of a corresponding plurality of identifiable object data fragments; and
   d) fragmenting said linear sequence of data elements utilizing a DNA sequence fragment generator module and one or more of a parametric sequence fragment generator module and a biometric sequence fragment generator module to generate a plurality of identifiable object data fragments each including a part of said linear sequence data elements, each of said plurality of identifiable object data fragments having a number of data elements corresponding to said numeric value of a corresponding one of said set of random numbers.

2. The computer implemented method of generating an identification element of claim 1, wherein obtaining an amount of identifiable object data as a linear sequence of data elements comprises obtaining an amount DNA sequence data, and wherein fragmenting said linear sequence of data elements to generate a plurality of identifiable object data fragments each including a part of said linear sequence of data elements having a number of data elements corresponding to said numeric value of said corresponding one of said first set of random numbers comprises fragmenting said amount of DNA sequence data to generate a plurality of DNA sequence fragments each including a part of said of DNA sequence data having a number of DNA data elements corresponding to said numeric value of said corresponding one of said set of random numbers.

3. The computer implemented method of generating an identification element of claim 2, wherein obtaining an amount of DNA sequence data comprises obtaining an amount of DNA sequence data selected from the group consisting of an amount of rRNA sequence data and mitochondrial DNA sequence data.

4. The computer implemented method of generating an identification element of claim 2, further comprising obtaining a second amount of identifiable object data as a second linear sequence of data elements.

5. The computer implemented method of generating an identification element of claim 4, further comprising generating a second set of random numbers each random number of said second set of random numbers having a numeric value.

6. The computer implemented method of generating an identification element of claim 5, further comprising fragmenting said second linear sequence of data elements to generate a second plurality of identifiable object data fragments each including a part of said second linear sequence of data elements having a number of data elements corresponding to said numeric value of a corresponding one of said second set of random numbers.

7. The computer implemented method of generating an identification element of claim 6, wherein said second linear sequence data comprises an amount of parametric data or an amount of biometric data and further comprising translating each said part of said second linear sequence of data elements utilizing a sequence translator module to correspondingly generate a second plurality of DNA sequence fragments each having a linear sequence of DNA data elements.

8. The computer implemented method of generating an identification element of claim 7, further comprising obtaining a third amount of identifiable object data as a third linear sequence of data elements.

9. The computer implemented method of generating an identification element of claim 8, further comprising generating a third set of random numbers each random number of said third set of random numbers having a numeric value.

10. The computer implemented method of generating an identification element of claim 9, further comprising fragmenting said third linear sequence of data elements to generate a third plurality of identifiable object data fragments each including a part of said third linear sequence of data elements having a number of data elements corresponding to said numeric value of a corresponding one of said third set of random numbers.

11. The computer implemented method of generating an identification element of claim 10, wherein said third linear sequence data comprises an amount of parametric data or an amount of biometric data and further comprising translating each said part of said third linear sequence of data elements to correspondingly generate a third plurality of DNA sequence fragments each having said linear sequence of DNA data elements.

12. The computer implemented method of generating an identification element of claim 11, further comprising embedding said third plurality of DNA sequence fragments said second plurality and said plurality of DNA sequence fragments utilizing an embedded sequence generator module to generate said identification element.

13. The computer implemented method of generating an identification element of claim 7, further comprising embedding said second plurality of DNA sequence fragments and said plurality of DNA sequence fragments utilizing an embedded sequence generator module to generate said identification element.

14. The computer implemented method of generating an identification element of claim 13, further comprising generating a vector data sequence.

15. The computer implemented method of generating an identification element of claim 14, further comprising translating said vector data sequence into vector DNA sequence having a linear sequence of DNA data elements utilizing a sequence translator module.

16. The computer implemented method of generating an identification element of claim 15, further comprising embedding said vector DNA sequence into said second plurality of DNA sequence fragments and said plurality of DNA sequence fragments to generate said identification element utilizing an embedded sequence generator module.

17. The computer implemented method of generating an identification element of claim 16, further comprising decoding said identification element utilizing a DNA sequence decoder module to retrieve at least a part of said first amount of identifiable object data.

18. The computer implemented method of generating an identification element of claim 16, further comprising decoding said identification element utilizing a DNA sequence decoder module to retrieve at least a part of said second amount of identifiable object data.

19. The computer implemented method of generating an identification element of claim 16, further comprising decoding said identification element utilizing a DNA sequence decoder module to retrieve at least a part of said third amount of identifiable object data.

20. The computer implemented method of generating an identification element of claim 16, further comprising decoding said identification element utilizing a DNA sequence decoder module to retrieve said vector element.

21. The computer implemented method of generating an identification element of claim 13, further comprising matching said identification element to an identifiable object.

22. The computer implemented method of generating an identification element of claim 21, further comprising allowing access to a searchable database based on matching said identification element to said identifiable object.

23. The computer implemented method of generating an identification element of any one of claim 13, 12, or 16, wherein said identification element comprises an embedded data DNA sequence.

* * * * *